United States Patent
Ruff et al.

(10) Patent No.: US 6,528,521 B2
(45) Date of Patent: Mar. 4, 2003

(54) TREATMENT OF ANTI-DEPRESSION DRUG-INDUCED SEXUAL DYSFUNCTION WITH APOMORPHINE

(75) Inventors: Dustin D. Ruff, Greenwood, IN (US); Renee J. Perdok, Gurnee, IL (US)

(73) Assignee: Tap Pharmaceutical Products, Inc., Lake Forest, IL (US)

( * ) Notice: Subject to any disclaimer, the term of this patent is extended or adjusted under 35 U.S.C. 154(b) by 0 days.

(21) Appl. No.: 09/993,782

(22) Filed: Nov. 14, 2001

(65) Prior Publication Data

US 2002/0115683 A1 Aug. 22, 2002

Related U.S. Application Data

(60) Provisional application No. 60/249,031, filed on Nov. 15, 2000.

(51) Int. Cl.$^7$ ............................................. A61K 31/473
(52) U.S. Cl. ..................................................... 514/284
(58) Field of Search .......................................... 514/284

(56) References Cited

U.S. PATENT DOCUMENTS 4,521,421 A * 6/1985 Foreman ..................... 514/267
5,756,483 A 5/1998 Merkus ....................... 514/58
5,770,606 A 6/1998 El-Rashidy et al. ......... 514/284
5,866,164 A 2/1999 Kuczynski et al. .......... 424/472
5,897,864 A 4/1999 Cohen ....................... 424/195.1
5,939,094 A 8/1999 Durif et al. ................. 424/448
5,945,117 A 8/1999 El-Rashidy et al. ......... 424/430

OTHER PUBLICATIONS

Marketletter of Jul. 17, 1995 (abstract).*

Wilson, E.K., Chemical & Engineering News, 76(26), pp. 29 (Jun. 29, 1998).*

* cited by examiner

Primary Examiner—Phyllis G. Spivack
(74) Attorney, Agent, or Firm—Wood, Phillips, Katz, Clark & Mortimer

(57) ABSTRACT

A method for treating sexual dysfunction that is caused by anti-depressant medication in a patient in need of such treatment, comprising administering a therapeutically effective amount of apomorphine, or a pharmaceutically acceptable salt thereof to said patient, is disclosed. The method may be utilized for patients taking anti-depressants such as tricyclic anti-depressants, monamine oxidase inhibitors or serotonin selective reuptake inhibitors.

9 Claims, No Drawings

TREATMENT OF ANTI-DEPRESSION DRUG-INDUCED SEXUAL DYSFUNCTION WITH APOMORPHINE

This application claims the benefit of Provisional application Ser. No. 60/249,031, filed Nov. 15, 2000.

FIELD OF THE INVENTION

The present invention is directed to a method for treating sexual dysfunction in a patient taking anti-depressant medication in need of such treatment comprising administering a therapeutically effective amount of apomorphine or a pharmaceutically acceptable salt thereof to said patient. The method may be utilized for patients taking anti-depressants such as tricyclic anti-depressants, monamine oxidase inhibitors or serotonin selective reuptake inhibitors.

BACKGROUND OF THE INVENTION

Depression is a chronic illness that affects people of all ages. Tricyclic antidepressants, monamine oxidase inhibitors, and selective serotonin reuptake inhibitors are classes of drugs which are prescribed for the treatment of depression. Tricyclic anti-depressants include imipramine hydrochloride, imipramine pamoate, amitriptyline hydrochloride, desipramine hydrochloride and protriptyline hydrochloride. Monamine oxidase inhibitors include isocarboxazid, phenelzine sulfate and tranylcypromine sulfate. Of the various classes of anti-depressants currently available, the selective serotonin reuptake inhibitors (SSRI's) are among the most successful.

SSRI's include fluoxetine, fluvoxamine, citalopram, cericlamine, femoxetine, ifoxetine, cyanodothiepin, seritraline, paroxetine and litoxetine. Anti-depressants have many undesirable side effects, such as disturbance of sexual function. Since sexual dysfunction is common in depression as part of the underlying disease, the use of a drug to treat depression which may further cause sexual dysfunction is particularly objectionable.

A variety of strategies have been reported in the management of SSRI-induced sexual dysfunction, including waiting for tolerance to develop, dosage reduction, drug holidays, substitution of another anti-depressant drug, and various augmentation strategies (addition of another drug) with $5-HT_2$, $5-HT_3$ and $\alpha_2$ adrenergic receptor antagonists, $5-HT_{1A}$ and dopamine receptor agonists and phosphodiesterase enzyme inhibitors, as disclosed by Rosen et al. in *J. Clin. Psychopharmacol.* Vol. 19, No 1, pp.67–84.

Augmentation strategies may include co-treatment with cyproheptadine, bethanecol, yohimbine, amantadine, alprazolam, chlordiazepoxide, clonazepam, diazepam or lorazepam according to Forman et al., "Drug-induced infertility and Sexual Dysfunction" in *Textbook of Erectile Dysfunction*, Oxford: Isis Medical Media Ltd, 1999, pp. 40–43; co-treatment with Ginkgo Biloba as disclosed in U.S. Pat. No. 5,897,864; or co-treatment with sidenafil, according to Fava et al., "An Open Trial of Oral Sildenafil in Antidepressant-Induced Sexual Dysfunction", *Psychother. Psychosom.*, 1998, 328–331.

Nevertheless, there is still a need for effective medications which can be used to treat sexual dysfunction in patients taking anti-depressants.

It is therefore an object of the present invention to provide a method for the treatment of sexual dysfunction in patients taking anti-depressants, to treat the condition potentially caused by the depression and exacerbated by the anti-depressant.

SUMMARY OF THE INVENTION

The present invention is directed to a method of treating sexual dysfunction in a patient taking anti-depressant medication in need of such treatment comprising administering a therapeutically effective amount of apomorphine or a pharmaceutically acceptable salt thereof to said patient. The anti-depressant medication may be a tricyclic anti-depressant, a monamine oxidase inhibitor or a serotonin-selective reuptake inhibitor. Preferably, the therapeutically effective amount of apomorphine is an amount wherein a concentration of apomorphine is attained within said patient's plasma of up to 10 nanograms per milliliter.

If the patient is male, the therapeutically effective amount may be an amount sufficient to induce an erection adequate for vaginal penetration. Alternatively, if the patient is female the therapeutically effective amount may be an amount sufficient to induce clitoral erectogenesis and vaginal engorgement. Preferably, the therapeutically effective amount is insufficient to produce emesis. However, if larger (potentially emesis-inducing) doses are required, the apomorphine may be co-administered with an emesis-inhibiting amount of an anti-emetic agent.

The anti-emetic agent may be nicotine, lobeline sulfate, metoclopramide, chlorpromazine, prochlorperazine, pipamazine, thiethylperazine, oxypendyl hydrochloride, domperidone, ondansetron, buclizine hydrochloride, cyclizine hydrochloride, dimenhydrinate, scopolamine, metopimazine, trimethobenzamide, benzauinamine hydrochloride or diphenidol hydrochloride.

In the method, apomorphine may administered intranasally, orally ingested, sublingually or administered by inhalation to the lungs. Moreover, the apomorphine may be administered as a pharmaceutically acceptable salt, preferably the hydrochloride salt.

DETAILED DESCRIPTION OF THE INVENTION

In males, the form of sexual dysfunction is erectile dysfunction. A normal erection occurs as a result of a coordinated vascular event in the penis. This is usually triggered neurally and consists of vasodilation and smooth muscle relaxation in the penis and its supplying arterial vessels. Arterial inflow causes enlargement of the substance of the corpora cavemosa. Venous outflow is trapped by this enlargement, permitting sustained high blood pressures in the penis sufficient to cause rigidity. Muscles in the perineum also assist in creating and maintaining penile rigidity. Erection may be induced centrally in the nervous system by sexual thoughts or fantasy, and is usually reinforced locally by reflex mechanisms. Erectile mechanics are substantially similar in the female for the clitoris.

Impotence or male erectile dysfunction is defined as the inability to achieve and sustain an erection sufficient for intercourse. Impotence in any given case can result from psychological disturbances (psychogenic), from physiological abnormalities in general (organic), from neurological disturbances (neurogenic), hormonal deficiencies (endocrine) or from a combination of the foregoing. Impotence may be hormonal, congenital, vascular or partial ability, among others.

These descriptions are not exact, however. There is currently no standardized method of diagnosis or treatment. As used herein, psychogenic impotence is defined as functional impotence with no apparent overwhelming organic basis. It may be characterized by an inability to have an erection in response to some stimuli (e.g., masturbation, spontaneous nocturnal, spontaneous early morning, video erotica, etc.) but not others (e.g., partner or spousal attention).

Females also can have sexual dysfunction that increases with age and is associated with the presence of vascular risk factors and onset of menopause. Some of the vascular and muscular mechanisms that contribute to penile erection in the male are believed to be similar vasculogenic factors in female genital response. It is known that in women, sexual arousal is accompanied by arterial inflow which engorges the vagina and increases vaginal lubrication and that the muscles in the perineum assist in achieving clitoral erection.

In the female, sexual dysfunction can arise from organic and psychogenic causes or from a combination of the foregoing. Female sexual dysfunction includes a failure to attain or maintain vaginal lubrication-swelling responses of sexual excitement until completion of the sexual activity. Organic female sexual dysfunction is known to be related in part to vasculogenic impairment resulting in inadequate blood flow, vaginal engorgement insufficiency and clitoral erection insufficiency.

Apomorphine ((R)-5,6,6a,7-tetrahydro-6-methyl-4H-dibenzo-[de,g]quinoline-10,11-diol) can be represented by the formula

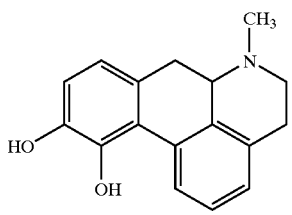

and exists in a free base form or as an acid addition salt. For the purposes of the present invention, apomorphine hydrochloride is preferred, however other pharmacologically acceptable salts thereof can be utilized as well.

Apomorphine can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzene sulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate and undecanoate salts. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Apomorphine has been disclosed as useful in intranasal formulations for the treatment of Parkinson's disease in U.S. Pat. No. 5,756,483.

Apomorphine transdermal administration has been disclosed in U.S. Pat. No. 5,939,094; and apomorphine in capsule form has been disclosed in U.S. Pat. No. 5,866,164.

Apomorphine is a dopamine receptor agonist that has a recognized use as an emetic when administered subcutaneously in about a 5 milligram dose. For the purposes of the present invention, apomorphine is administered in an amount sufficient to excite cells in the mid-brain region of the patient but with minimal side effects. This cell excitation is believed to be part of a cascade of stimulation that is likely to include neurotransmission with serotonin, dopamine and oxytocin.

The dopamine receptors in the mid-brain region of a patient can be stimulated to a degree sufficient to cause an erectile response without inducing nausea by the administration, preferably sublingually, of apomorphine so as to maintain a plasma concentration of apomorphine of no more than about 5.5 nanograms per milliliter (5.5 ng/ml). The sublingual administration usually takes place over a period of time in the range of about 2 to about 10 minutes, or longer. The amount of apomorphine administered sublingually over this time period preferably is in the range of about 25 micrograms per kilogram ($\mu$g/kg) of body weight to about 60 $\mu$g/kg of body weight.

In sensitive patients experiencing nausea, the onset of nausea can be obviated or delayed by delivering apomorphine at a controlled dissolution rate so as to provide circulating serum levels and midbrain tissue levels of apomorphine less than 5.5 nanograms/mL. When apomorphine is administered at or near the higher amounts of the aforementioned dosage range, the likelihood of the onset of nausea can be reduced by concurrent administration of a ganglionic agent (inhibitor of ganglionic response and anti-emetic agent) such as nicotine or lobeline sulfate. For this purpose, the weight ratio of apomorphine to ganglionic agent is in the range of about 10 to 1.

Other anti-emetic agents that can be used in conjunction with apomorphine are anti-dopaminergic agents such as metoclopramide, and the phenothiazines, e.g., chlorpromazine, prochlorperazine, pipamazine, thiethylperazine and oxypendyl hydrochloride among others. Also suitable are the serotonin (5-hydroxytryptamine or 5-HT) antagonists such as domperidone, ondansetron (commercially available as the hydrochloride salt under the designation ZOFRAN) among others, the histamine antagonists such as buclizine hydrochloride, cyclizine hydrochloride, dimenhydrinate (DRAMAMINE) among others, the parasympathetic depressants such as scopolamine, as well as other anti-emetics such as metopimazine, trimethobenzamide, benzauinamine hydrochloride, and diphenidol hydrochloride among others.

The term "co-administered" used herein indicates treatment with two or more pharmacological agents together in a single unit dosage form or alternatively, in two or more separate unit dosage forms, one immediately following the other.

The apomorphine according to the invention can be administered as a nasal spray, nasal drop, suspension, gel, ointment, cream or powder. The administration of the nasal composition may also take place using a nasal tampon or nasal sponge.

Powders can be administered using a nasal insufflator. Powders can also be used in such a manner that they are placed in a capsule. The capsule is set in an inhalation or insufflation device. A needle is penetrated through the capsule to make pores at the top and the bottom of the capsule, and air is sent to blow out the powder particles. Powder formulations can also be administered in a jet-spray of an inert gas or suspended in liquid organic fluids.

Sublingual apomorphine dosage forms, usually containing about 2.5 to about 10 milligrams of apomorphine, have been found to be effective in male patients suffering from psychogenic erectile dysfunction for the induction and maintenance of an erection sufficient for intercourse (i.e., vaginal penetration) without nausea or other undesirable side effects. The apomorphine is administered sublingually, preferably about 15 to about 20 minutes prior to sexual activity, and so as to maintain a predetermined circulating serum levels and mid-brain tissue levels of apomorphine during the period of sexual activity sufficient to induce an erection adequate for vaginal penetration but less than the amount that induces nausea. The plasma concentration of apomorphine should be maintained at no more than about 5.5 nanograms per milliliter, preferably about 0.3 to about 4 nanograms per milliliter, and more preferably about 1 to about 2 nanograms per milliliter.

Apomorphine may be included in a pharmaceutical composition comprising apomorphine and a physiologically tolerable diluent. The present invention includes apomorphine and salts thereof as described above formulated into compositions together with one or more non-toxic physiologically tolerable or acceptable diluents, carriers, adjuvants or vehicles that are collectively referred to herein as diluents for intranasal delivery or for oral administration in solid or liquid form.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars and sodium chloride, among others.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, among others.

Useful intranasal formulations contain a stabilizer and a surfactant. Among the pharmaceutically acceptable surfactants are polyoxyethylene castor oil derivatives, such as polyoxyethylene-glycerol-triricinoleate, also known as polyoxyl 35 castor oil (CREMOPHOR EL), or poloxyl 40 hydrogenated castor oil (CREMOPHOR RH40) both available from BASF Corp.; mono-fatty acid esters of polyoxyethylene (20) sorbitan, such as polyoxyethylene (20) sorbitan monolaurate (TWEEN 80), polyoxyethylene monostearate (TWEEN 60), polyoxyethylene (20) sorbitan monopalmitate (TWEEN 40), or polyoxyethylene 20 sorbitan monolaurate (TWEEN 20) all available from ICI Surfactants of Wilmington, Del.); polyglyceryl esters, such as polyglyceryl oleate; and polyoxyethylated kernel oil (LABRAFIL, available from Gattefosse Corp.) Preferably, the surfactant will be between about 0.01% and 10% by weight of the pharmaceutical composition.

Among the pharmaceutically useful stabilizers are antioxidants such as sodium sulfite, sodium metabisulfite, sodium thiosulfate, sodium formaldehyde sulfoxylate, sulfur dioxide, ascorbic acid, isoascorbic acid, thioglycerol, thioglycolic acid, cysteine hydrochloride, acetyl cysteine, ascorbyl palmitate, hydroquinone, propyl gallate, nordihydroguaiaretic acid, butylated hydroxytoluene, butylated hydroxyanisole, alpha-tocopherol and lecithin. Preferably, the stabilizer will be between about 0.01% and 5% by weight of the pharmaceutical composition.

Chelating agents such as ethylene diamine tetraacetic acid, its derivatives and salts thereof, dihydroxyethyl glycine, citric acid and tartaric acid among others may also be utilized.

Proper fluidity can be maintained, for example, by the use of coating materials such as lecithin, by the maintenance of the required particle size in the case of dispersions and by the use of surfactants.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

The apomorphine may also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The ability of apomorphine to ameliorate anti-depressant-induced sexual dysfunction is described in detail hereinafter in the Examples. These Examples are presented to describe preferred embodiments and utilities of the invention and are not meant to limit the invention unless otherwise stated in the claims appended hereto.

EXAMPLE 1

A crossover study of 1500 patients in a home-use trial of apomorphine on male patients was performed. Out of the 1500 patients, 47 were taking selective serotonin reuptake inhibitors, as indicated in Table 1.

TABLE 1

| SSRI Drug Taken | No. patients taking drug |
|---|---|
| PROZAC | 22 |
| ZOLOFT | 13 |
| PAXIL | 12 |

In the crossover study, a 2–4 week baseline period was used to evaluate subjects. After this time, during an initial four week treatment period, subjects received either a placebo or apomorphine, without knowing whether or not they had received the active medication. The dosage was either 2, 4, 5 or 6 mg. This initial treatment period was followed by a 24–96 hour washout period, in which no medication was taken. Subsequently, a second four week treatment period, subjects who previously had received apomorphine, were given a placebo, and subjects who previously had received the placebo were given apomorphine. Subject were to attempt coitus once each week after taking a single tablet of apomorphine sublingually. After each attempt, the subject and his partner completed a sexual function questionnaire which was later evaluated and used for final statistical analysis. In the analysis, the data for patients receiving 2, 4, 5 or 6 mg dosages was pooled.

In response to the question of whether an erection firm enough for intercourse had been attained, patients on SSRI's given apomorphine responded that 48% of attempts were successful, while patients on SSRI's given a placebo responded that only 26% of attempts were successful.

In response to the question of whether the attempt resulted in intercourse, patients on SSRI's given apomorphine responded that 47.6% of attempts were successful, while patients on SSRI's given a placebo responded that only 23.4% of attempts were successful.

Therefore, after taking apomorphine, twice as many patients on SSRI drugs were able to have intercourse. The data presented thus demonstrates that the administration of apomorphine to patients who are taking anti-depressants and experiencing sexual dysfunction is successful in treating or ameliorating the condition.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby. Changes can be made in the composition, operation and arrangement of the method of the present invention described herein without departing from the concept and scope of the invention as defined in the following claims:

We claim:

1. A method of treating sexual dysfunction that is caused by anti-depressant medication in a patient in need of such treatment comprising administering a therapeutically effective amount of apomorphine, or a pharmaceutically acceptable salt thereof, to said patient.

2. The method of claim 1 wherein said anti-depressant medication is a tricyclic anti-depressant, a monamine oxidase inhibitor or a serotonin-selective reuptake inhibitor.

3. The method of claim 1 wherein said patient is male and said therapeutically effective amount is an amount sufficient to induce an erection adequate for vaginal penetration.

4. The method of claim 1 wherein said patient is female and said therapeutically effective amount is an amount sufficient to induce clitoral erectogenesis and vaginal engorgement.

5. The method of claim 1 wherein said therapeutically effective amount is an amount wherein a concentration of apomorphine is attained within said patient's plasma of up to 10 nanograms per milliliter.

6. The method of claim 1 wherein said apomorphine is administered intranasally, orally ingested, sublingually or administered by inhalation to the lungs.

7. The method of claim 1 wherein said apomorphine is administered as the hydrochloride salt.

8. The method of claim 1 wherein said apomorphine is co-administered with an emesis-inhibiting amount of an anti-emetic agent.

9. The method of claim 8 wherein said anti-emetic agent is selected from the group consisting of nicotine, lobeline sulfate, metoclopramide, chlorpromazine, prochlorperazine, pipamazine, thiethylperazine, oxypendyl hydrochloride, domperidone, ondansetron, buclizine hydrochloride, cyclizine hydrochloride, dimenhydrinate, scopolamine, metopimazine, trimethobenzamide, benzauinamine hydrochloride and diphenidol hydrochloride.

* * * * *